United States Patent
Nakajima et al.

(10) Patent No.: US 11,044,563 B2
(45) Date of Patent: Jun. 22, 2021

(54) FILM SURFACE SOUND RECEIVING TYPE SOUND SENSOR MODULE

(71) Applicant: JAPAN AVIATION ELECTRONICS INDUSTRY, LIMITED, Tokyo (JP)

(72) Inventors: Shinichiro Nakajima, Tokyo (JP); Ryosuke Mitsui, Tokyo (JP); Junya Sato, Tokyo (JP); Atsushi Tanaka, Tokyo (JP); Noriyuki Mishina, Tokyo (JP)

(73) Assignee: JAPAN AVIATION ELECTRONICS INDUSTRY, LIMITED, Tokyo (JP)

( * ) Notice: Subject to any disclaimer, the term of this patent is extended or adjusted under 35 U.S.C. 154(b) by 27 days.

(21) Appl. No.: 16/473,410

(22) PCT Filed: Nov. 10, 2017

(86) PCT No.: PCT/JP2017/040586
§ 371 (c)(1),
(2) Date: Jun. 25, 2019

(87) PCT Pub. No.: WO2018/146879
PCT Pub. Date: Aug. 16, 2018

(65) Prior Publication Data
US 2020/0145763 A1    May 7, 2020

(30) Foreign Application Priority Data

Feb. 8, 2017   (JP) .............................. JP2017-021394

(51) Int. Cl.
*H04R 19/04*   (2006.01)
*H04R 1/04*    (2006.01)
(Continued)

(52) U.S. Cl.
CPC ............... *H04R 19/04* (2013.01); *H04R 1/04* (2013.01); *H04R 7/04* (2013.01); *H05K 1/028* (2013.01);
(Continued)

(58) Field of Classification Search
CPC ........ H04R 19/04; H04R 1/04; H04R 19/005; H04R 2201/003
See application file for complete search history.

(56) References Cited

U.S. PATENT DOCUMENTS

| | | | |
|---|---|---|---|
| 2004/0061543 A1 | 4/2004 | Nam et al. | |
| 2004/0142603 A1* | 7/2004 | Walker | H01L 25/18 439/701 |

(Continued)

FOREIGN PATENT DOCUMENTS

| | | |
|---|---|---|
| CN | 1765161 A | 4/2006 |
| CN | 102387456 A | 3/2012 |

(Continued)

OTHER PUBLICATIONS

Office Action issued in Taiwan family member Patent Appl. No. 106142329, dated Dec. 12, 2018, along with an English-language translation thereof.

(Continued)

*Primary Examiner* — Sunita Joshi
(74) *Attorney, Agent, or Firm* — Greenblum & Bernstein, P.L.C.

(57) ABSTRACT

A base member with wiring and a microphone are provided. In the base member with wiring, an insulation adhesive layer, which is elastically deformable, is provided on one surface of a film, which has flexibility, and a conductor pattern is formed on the insulation adhesive layer. The microphone is mounted on the base member with wiring. A terminal of the microphone is in touch with the conductor pattern in face-to-face manner, and a part, on which the terminal is not formed, of a surface of the microphone and a part, on which the conductor pattern is not formed, of a (Continued)

surface of the insulation adhesive layer are bonded and mechanically coupled with each other.

6 Claims, 6 Drawing Sheets

(51) Int. Cl.
    *H04R 7/04*     (2006.01)
    *H05K 1/02*     (2006.01)
    *H05K 1/18*     (2006.01)

(52) U.S. Cl.
    CPC ....... *H05K 1/189* (2013.01); *H04R 2201/003* (2013.01); *H05K 2201/10083* (2013.01)

(56) References Cited

U.S. PATENT DOCUMENTS

| | | |
|---|---|---|
| 2006/0169485 A1 | 8/2006 | Kawaguchi et al. |
| 2013/0251892 A1 | 9/2013 | Ho et al. |
| 2014/0044297 A1* | 2/2014 | Loeppert .................. H04R 1/08 381/355 |
| 2017/0374441 A1 | 12/2017 | Hoekstra et al. |

FOREIGN PATENT DOCUMENTS

| | | |
|---|---|---|
| CN | 203368716 U | 12/2013 |
| CN | 104796833 A | 7/2015 |
| CN | 205071257 U | 3/2016 |
| JP | H06-310832 A | 11/1994 |
| JP | 2002-271001 A | 9/2002 |
| JP | 2015-029182 A | 2/2015 |
| JP | 2016-209623 A | 12/2016 |
| TW | 200425768 A | 11/2004 |
| TW | 201624642 A | 7/2016 |

OTHER PUBLICATIONS

Search Report issued in WIPO Patent Application No. PCT/JP2017/040586, dated Jan. 30, 2018.
Office Action issued in China family member Patent Appl. No. 201780079525.0, dated Dec. 16, 2019, along with an English translation thereof.

* cited by examiner

FILM SURFACE SOUND RECEIVING TYPE SOUND SENSOR MODULE

TECHNICAL FIELD

The present invention relates to a sound sensor module and especially relates to a film surface sound receiving type sound sensor module which receives sound through a surface of a film which is attached to a surface of a solid which is a sound detection object.

BACKGROUND ART

FIG. 1A illustrates a configuration in which a microphone is mounted on a circuit board and which is described in Patent Literature 1. FIG. 1B illustrates a back surface of the microphone and FIG. 1C illustrates the circuit hoard which is partially enlarged.

The microphone 12 mounted on the circuit hoard 11 has a microphone sound hole 12a on a side facing the circuit hoard 11. The circuit board 11 has a board sound hole 11a formed to be aligned with the microphone sound hole 12a. On the back surface of the microphone 12, a ground land 13a, an output signal line land 13b, and a DC bias land 13c are formed as a microphone side land 13, while on the circuit board 11, a board side land 14, which is to be connected with the microphone side land 13 by soldering, is formed on a position corresponding to the microphone side land 13. The hoard side land 14 is composed of a ground land 14a, an output signal line land 14b, and a DC bias land 14c.

The microphone 12 captures external sound through the board sound hole 11a and the microphone sound hole 12a. The microphone 12 is assumed to be a micro electro mechanical system (MEMS) microphone, which can be mounted on a surface of a printed circuit board (PCB), a flexible circuit board, and the like by soldering, in this example.

Meanwhile, FIGS. 2A and 2B illustrate an array-shaped sound collection sensor device described in Patent Literature 2.

The array-shaped sound collection sensor device 20 includes a sheet-shaped soft support body 21, and a small microphone 23 is fixed on an inner bottom surface of each of cavities 22 formed on one surface of the sheet-shaped soft support body 21. The inner bottom surface is formed such that a hole to be the cavity 22 is formed in soft resin (soft urethane molding resin having high adhesion, for example) 21a by penetrating the soft resin 21a in the thickness direction of the soft resin 21a and one opening of the cavity 22 is closed by bonding a rubber sheet 21b on one surface of the soft resin 21a. On a surface, which is an opposite surface to the surface facing the cavities 22, of the rubber sheet 21b, amplifier circuit ICs 24 are fixed on positions corresponding to respective microphones 23 and are electrically connected to respective corresponding microphones 23.

This array-shaped sound collection sensor device 20 is used in a shunt stenosis diagnosis support system and a use state thereof is illustrated in FIG. 2C. The sheet-shaped soft support body 21 is put so that the openings of the cavities 22 face skin of a front arm of a subject. In FIG. 2C, 25 denotes a press band 25 for fixing the array-shaped sound collection sensor device 20. On the press band 25, hook and loop fasteners 26a and 26b are provided.

PRIOR ART LITERATURE

Patent Literature

Patent Literature 1: Japanese Patent Application Laid Open No. 2015-29182
Patent Literature 2: Japanese Patent Application Laid Open No. 2016-209623

SUMMARY OF THE INVENTION

Problems to be Solved by the Invention

Here, sound information becomes complex in accordance with interference, resonance, Doppler effect, and the like which depend not only on a position of a sound source but also on a propagation path and a medium through which sound propagates. Therefore, it is necessary to receive sound not by a point hut through a surface so as to comprehensively detect sound information.

In order to sensitively receive sound emitted from a solid through a surface, such method is conceivable that a microphone is mounted on a base member, which closely adheres to a surface of the solid, and the base member is brought into close contact with the surface of the solid, for example. When it is considered that such type of sound sensor module is repeatedly used with respect to various kinds of solids, the base member needs to be deformable with respect to various shapes of the various kinds of solids and the whole of the sound sensor module needs to be highly resistant to repeated use accompanied with various deformation and needs to be able to maintain highly-accurate and stable detecting performance. Further, it is also important that a base member can be selected depending on application so as to cope with various applications.

It can be said that both of the configuration, in which the microphone 12 is mounted on the circuit board 11 and which is illustrated in FIG. 1A as related art, and the configuration, in which the microphones 23 are fixed on the sheet-shaped soft support body 21 and which is illustrated in FIGS. 2A and 2B as related art, are the configuration in which a microphone is mounted on a deformable base member if it is assumed that the circuit board 11 illustrated in FIG. 1A is a flexible circuit board. However, soldering is employed for connecting the circuit board 11 and the microphone 12 in the configuration of FIGS. 1A and 1n this configuration, there is a cavity in a path from a surface of a solid to the microphone 12 (the microphone sound hole 12a) when the circuit board 11 is attached to the surface of the solid which is a sound detection object, for example.

Meanwhile, since the microphone 23 is fixed on the inner bottom surface of the cavity 22 which is closed by a detection object, there is a cavity in a path from a surface of a solid which is the detection object to the microphone 23 also in the configuration of FIGS. 2A and 2B.

Solder connection is employed as described above in the configuration for mounting a microphone on a base member, requiring the base member to have heat resistance. Accordingly, employable base members are limited and a base member having no heat resistance cannot be used.

Further, it cannot be said that connection and fixation by soldering are highly resistant to a load of stress, which variously changes through repeated use accompanied with various deformation, and vibration of sound input, and thus, the connection and fixation by soldering cause an occurrence of connection failure.

Further, in the case where there is a cavity in a path from a surface of a solid which is a detection object to a microphone and the cavity deforms along with deformation of a base member, this causes change in a sound propagation property and an occurrence of noise, inhibiting highly-accurate detection.

An object of the present invention is to provide a film surface sound receiving type sound sensor module in which even film having no heat resistance, for example, can be used as a base member and which is highly resistant to repeated use accompanied with various deformation, does not depend on shape change, and is capable of exhibiting highly-accurate and stable detecting performance.

Means to Solve the Problems

According to the present invention, a film surface sound receiving type sound sensor module includes: a base member with wiring in which an insulation adhesive layer, which is elastically deformable, is provided on one surface of a film, which has flexibility, and a conductor pattern is formed on the insulation adhesive layer; and a microphone that is mounted on the base member with wiring. A terminal of the microphone is in touch with the conductor pattern in face-to-face manner, and a part, on which the terminal is not formed, of a surface of the microphone and a part, on which the conductor pattern is not formed, of a surface of the insulation adhesive layer are bonded and mechanically coupled with each other.

Effects of the Invention

According to the present invention, since the microphone can be mounted without using soldering, that is, without heat, a film for through-a-surface sound reception is not required to have heat resistance. On this point, there is less limitation in film materials and thus films made of various kinds of materials can be used depending on application.

Further, the microphone is bonded and mechanically coupled with the insulation adhesive layer of the base member with wiring, and the terminal of the microphone and the conductor pattern of the base member with wiring are pressed and connected with each other by an elastic restoring force of the insulation adhesive layer. This configuration can provide a connection state which is highly-resistant and stable with respect to a load of stress, which variously changes due to repeated use accompanied with various deformation of the base member with wiring, and vibration of sound input, compared to soldering connection.

Further, there is no cavity, which causes change in a sound propagation property and an occurrence of noise along with shape change, in a path from the film attached on a surface of a solid which is a sound detection object to the microphone. Accordingly, a highly-accurate and stable detection performance can be obtained.

DETAILED DESCRIPTION OF THE EMBODIMENT

An embodiment of the present invention will be described below.

Figure 1B:
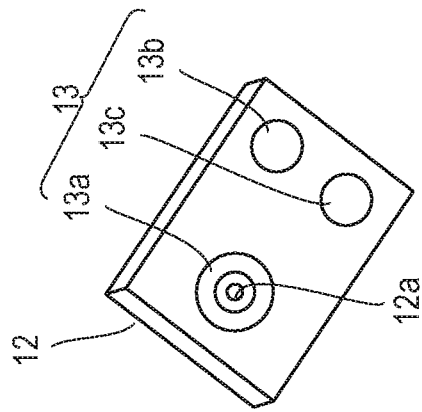
FIG. 1B is a perspective view of the microphone illustrated in FIG. 1A.
Figure 1C:
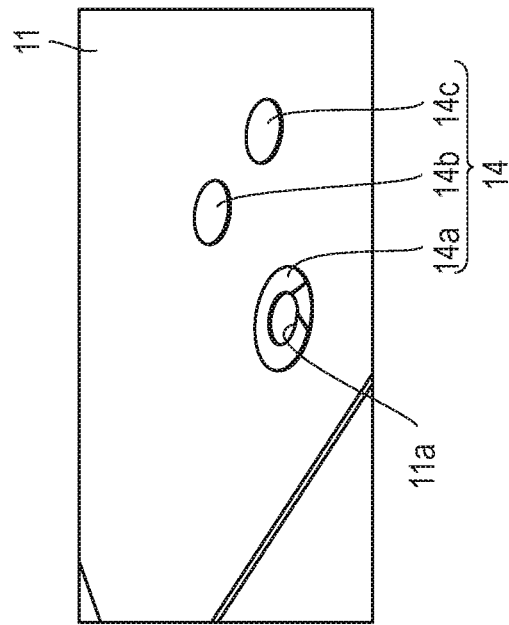
FIG. 1C is a partial enlarged perspective view of the circuit board illustrated in FIG. 1A.
Figure 1A:
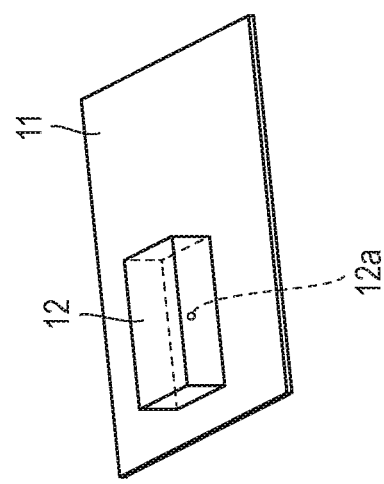
FIG. 1A is a perspective view illustrating the conventional configuration in which a microphone is mounted on a circuit board.
Figure 2A:
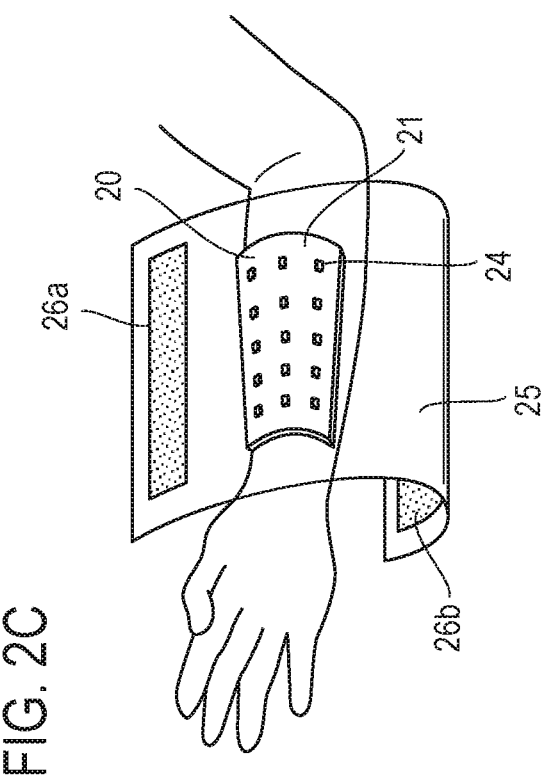
FIG. 2A is a perspective view illustrating an array-shaped sound collection sensor device of a related art.
Figure 2B:
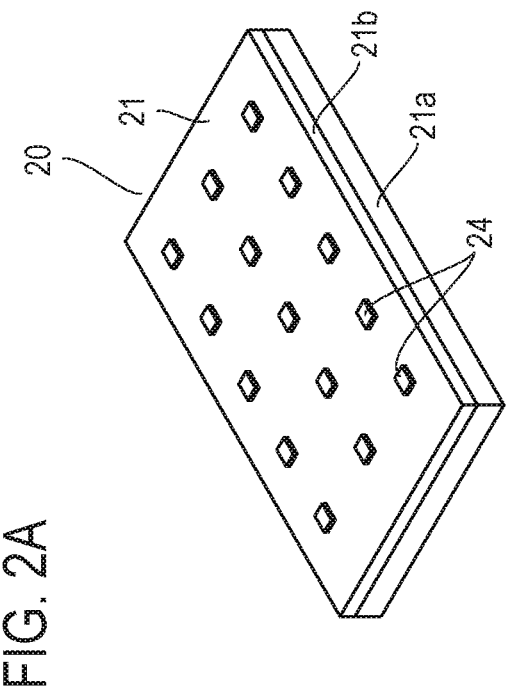
FIG. 2B is a partial enlarged sectional view of the array-shaped sound collection sensor device illustrated in FIG. 2A.
Figure 2C:
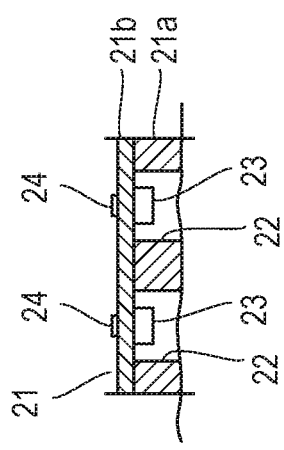
FIG. 2C is a drawing illustrating a use state of the array-shaped sound collection sensor device illustrated in FIG. 2A.
Figure 3A:
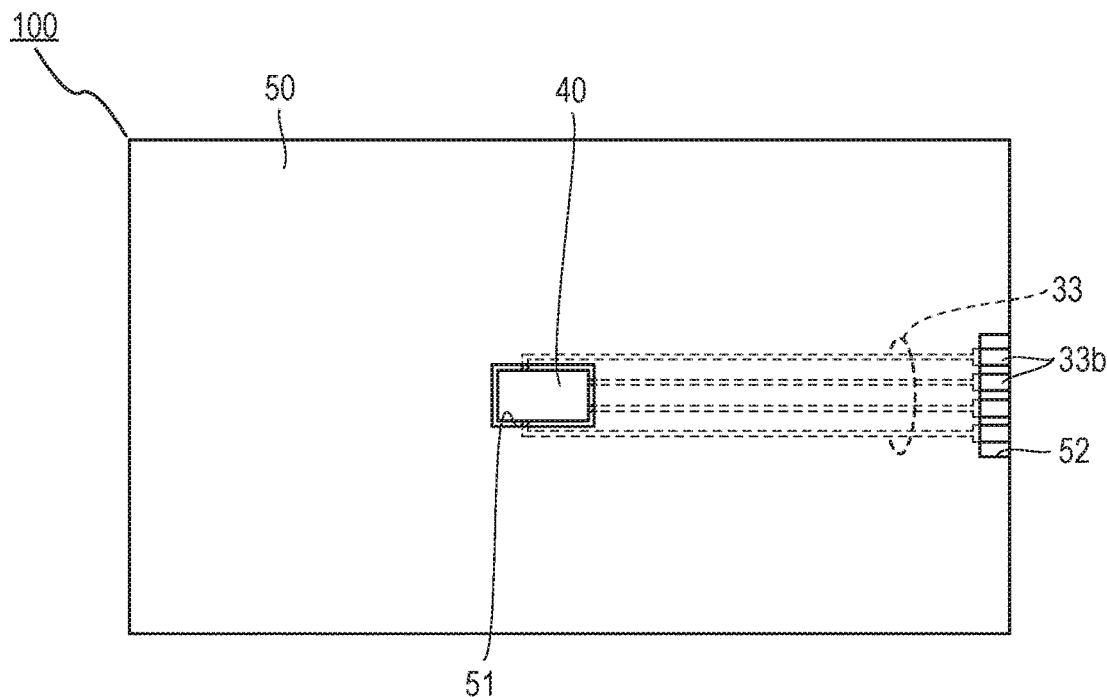
FIG. 3A is a plan view illustrating an embodiment of a film surface sound receiving type sound sensor module according to the present invention.
Figure 3B:
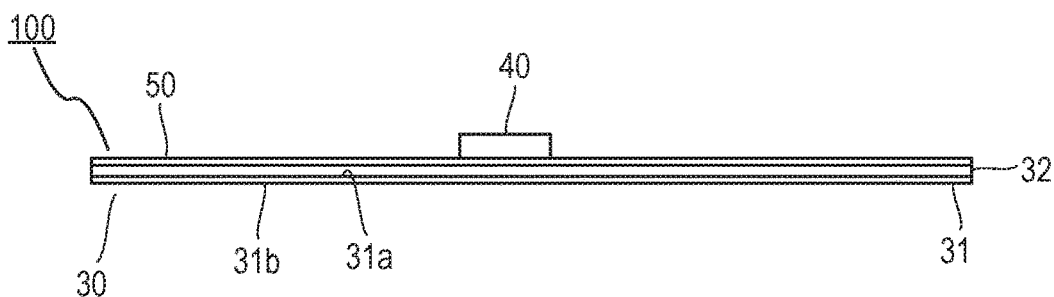
FIG. 3B is an elevational view of the film surface sound receiving type sound sensor module illustrated in FIG. 3A.
Figure 3C:
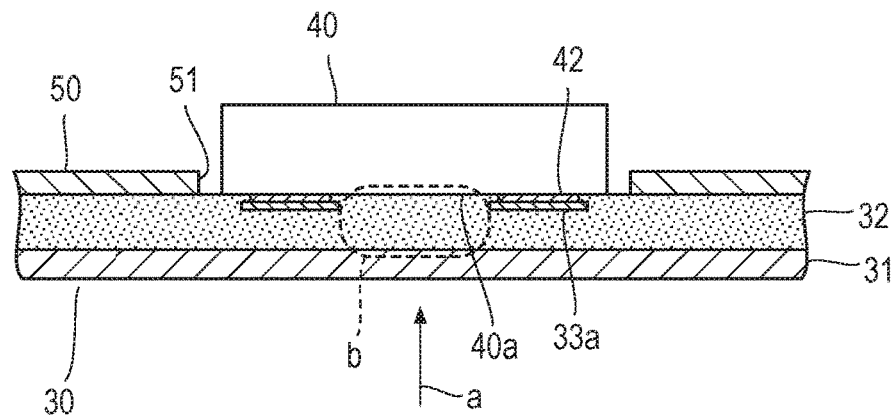
FIG. 3C is a partial enlarged sectional view of the film surface sound receiving type sound sensor module illustrated in FIG. 3A.
Figure 4A:
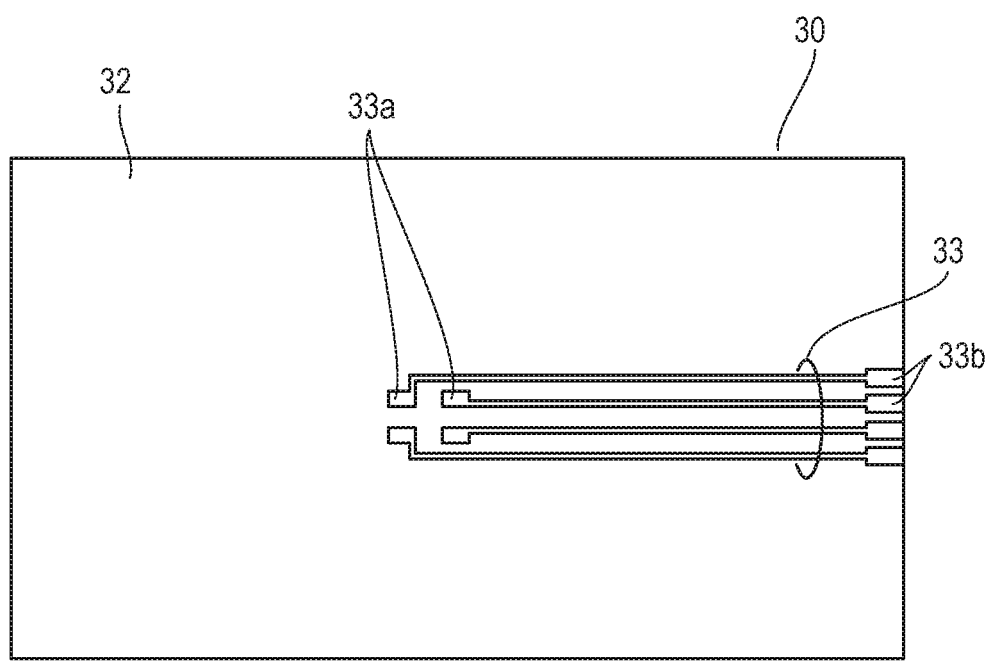
FIG. 4A is a plan view of a base member with wiring illustrated in FIG. 3B.
Figure 4B:
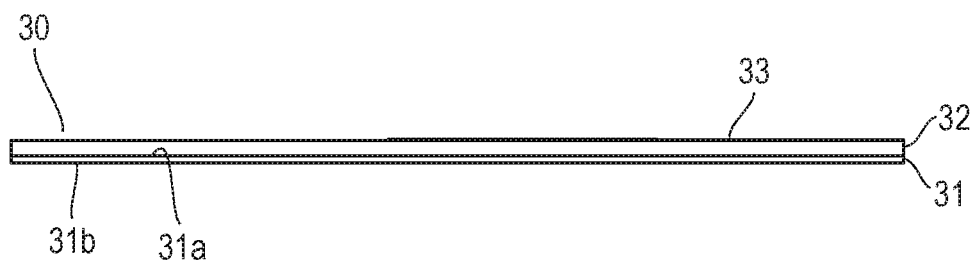
FIG. 4B is an elevational view of the base member with wiring illustrated in FIG. 4A.
Figure 5A:
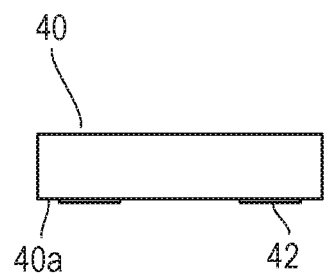
FIG. 5A is an elevational view of the microphone illustrated in FIG. 3A.
Figure 5C:
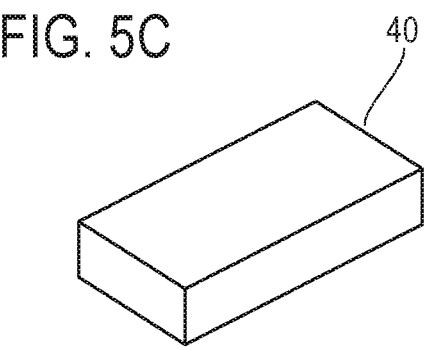
FIG. 5C is a perspective view of the microphone illustrated in FIG. 5A.
Figure 5B:
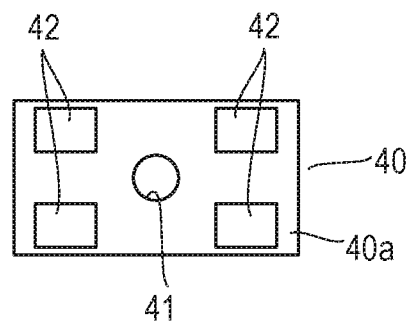
FIG. 5B is a bottom view of the microphone illustrated in FIG. 5A.

FIGS. 3A to 3C illustrate an embodiment of a film surface sound receiving type sound sensor module according to the present invention. This film surface sound receiving type sound sensor module 100 is composed of a base member with wiring 30, a microphone 40 mounted on the base member with wiring 30, and a cover film 50 in this example. FIGS. 4A and 4B illustrate details of the base member with wiring 30 and FIGS. 5A to 5C illustrate details of the microphone 40.

As illustrated in FIGS. 4A and 4B, the base member with wiring 30 is configured such that an insulation adhesive layer 32 is provided on one surface 31a of a film 31 and a conductor pattern 33 is formed on the insulation adhesive layer 32. The film 31 has flexibility and is assumed to form a larger (larger-area of) rectangular shape than that of the microphone 40, in this example. The insulation adhesive layer 32 elastically deforms when the insulation adhesive layer 32 is pressed and the insulation adhesive layer 32 is provided throughout the whole surface of one surface 31a of the film 31.

A conductor pattern 33 is formed to have four lines in this example, A land 33a for the microphone 40 is formed on each of one ends of the four conductor patterns 33 and a land 33b for connection with the outside (external circuit) is formed on each of the other ends. The four lands 33a for the microphone 40 are positioned in the center of the base member with wiring 30, and the lands 33b for external connection are positioned on the central part on one short side of the base member with wiring 30 in a manner to align along the short side.

In the above-described configuration, polyethylene terephthalate (PET), for example, can be used for a material of the film 31.

Examples of an insulation adhesive constituting the insulation adhesive layer 32 include polyester-based, polyurethane-based, acrylic-based, epoxy-based, phenolic-based, silicone-based, polyolefin-based, polyimide-based, vinyl-based, and natural polymer-based polymers. The above-mentioned polymers may be singly used or may be used in combination.

Further, in order to improve adhesion and a mechanical property, polyester-based, polyurethane-based, acrylic-based, epoxy-based, phenolic-based, silicone-based, polyolefin-based, polyimide-based, and vinyl-based monomers and oligomers, for example, may be mixed with the above-mentioned polymers.

The conductor pattern 33 is formed by printing with silver paste (silver ink), for example.

The microphone 40 is assumed to be a MEMS microphone which is manufactured by employing the MEMS technology in this example. The microphone 40 is provided with a sound hole 41 formed on a bottom surface 40a thereof and further provided with four terminals 42 in this example, as illustrated in FIG. 5B. The four terminals 42 are respectively an output terminal, a ground terminal, a power source terminal, and a gain adjustment terminal.

Figure 6:
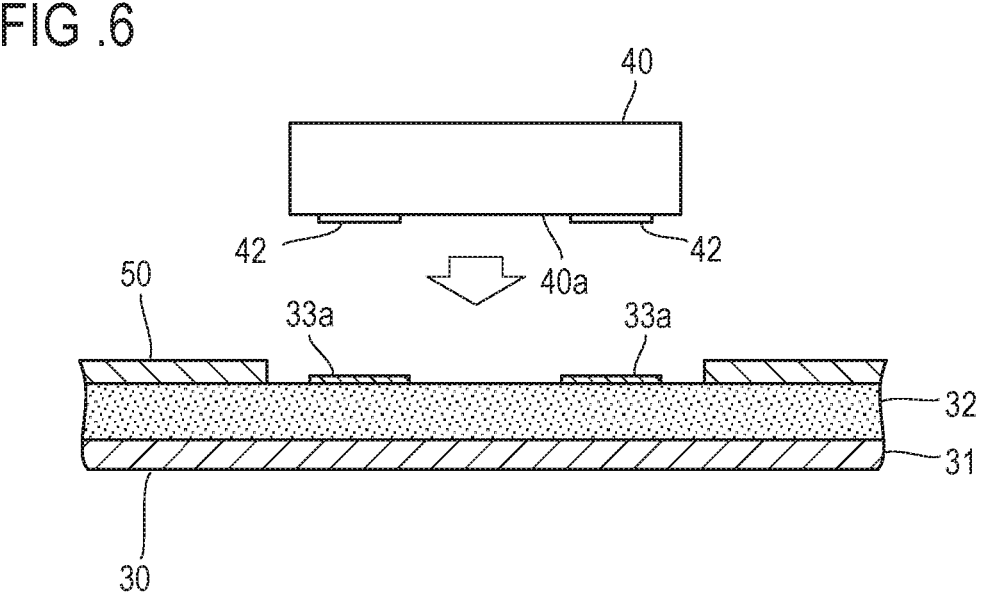
FIG. 6 is a drawing illustrating assembling of the film surface sound receiving type sound sensor module illustrated in FIGS. 3A to 3C.

FIG. 6 illustrates a state that the microphone 40 is mounted on the base member with wiring 30. The microphone 40 is mounted by compressing the microphone 40 against the insulation adhesive layer 32 in such a manner that the four terminals 42 are positioned and pressed respectively on the lands 33a of the four conductor patterns 33 formed on the insulation adhesive layer 32.

The terminals 42 of the microphone 40 are directly brought into contact with the lands 33a in face-to-face manner and electrically connected with the lands 33a respectively, and part, on which the terminals 42 are not formed, of the bottom surface 40a of the microphone 40 is bonded and mechanically coupled with the insulation adhesive layer 32, as illustrated in FIG. 3C. That is, mechanical coupling between the insulation adhesive layer 32, on which the conductor pattern 33 is formed, and the microphone 40 is performed such that part, on which the terminals 42 are not formed, of the surface of the microphone 40 and part, on which the conductor pattern 33 is not formed, of the surface of the insulation adhesive layer 32 are bonded with each other, in this example.

Here, the insulation adhesive layer 32 elastically deforms and adheres when the insulation adhesive layer 32 is pressed, and thereby an elastic restoring force of the insulation adhesive layer 32 contributes as a load in a direction in which the terminals 42 of the microphone 40 and the lands 33a of the conductor pattern 33 are pressed and bonded with each other, being able to provide a favorable connecting state between the terminals 42 and the lands 33a.

The cover film 50 is disposed on the surface, on which the conductor pattern 33 is formed, of the base member with wiring 30. On the cover film 50, a window 51 and a cutout 52 are formed respectively on a part corresponding to the position of the microphone 40 and a part corresponding to the positions of the external connection lands 33b of the conductor pattern 33, as illustrated in FIG. 3A. Thus, the surface, on which the conductor pattern 33 is formed, of the base member with wiring 30 is covered by the cover film 50 excluding the part on which the microphone 40 is positioned and the part on which the four lands 33b are positioned, as illustrated in FIGS. 3A to 3C.

The cover film 50 is assumed to have flexibility as is the case with the film 31 which is a base of the base member with wiring 30, and the cover film. 50 is made of the same material as that of the film 31.

The film surface sound receiving type sound sensor module 100 having the above-described configuration is used by attaching a surface, on which the microphone 40 is not mounted, of the base member with wiring 30, that is, an opposite surface 31b of one surface 31a, on which the insulation adhesive layer 32 is provided, of the film 31, on a surface of a solid which is a sound detection object. In the case where the film 31 closely adheres along a surface of a solid, the film 31 may be merely placed on the solid. On the other hand, in the case where a surface of a solid does not have a simple shape and therefore close adherence is impossible or difficult, the film 31 is brought into close contact with the surface of the solid by using an adhesive, for example.

According to the film surface sound receiving type sound sensor module 100 described above, the microphone 40 is mounted on the base member with wiring 30 without using soldering, that is, the mounting is performed without using any heat, Therefore, even a material having no heat resistance can be used as a material of the film 31 and films made of various kinds of materials can be used depending on application. The shape and the size of the film 31 are arbitrarily selected depending on application.

Further, connection and fixation (mechanical coupling) between the base member with wiring 30 and the microphone 40 by bonding exhibit high resistance to a load of stress, which variously changes due to repeated use accompanied with various deformation of the base member with wiring 30, and vibration of sound input compared to connection and fixation by soldering, and accordingly do not cause an occurrence of connection failure. Thus, a stable connection state can be obtained.

Further, since the film 31 is brought into close contact with a surface of a solid which is a sound detection object, there is no cavity in a path from the surface of the solid which is the detection object to the microphone 40, that is, there is no cavity which deforms following deformation of the base member with wiring 30 and causes change in a sound propagation property and an occurrence of noise. Therefore, highly-accurate and stable sound detection can be performed without depending on shape change.

Here, an insulation adhesive constituting the insulation adhesive layer 32 may have an ultraviolet curing property. In this case, ultraviolet rays are radiated from the direction illustrated by the arrow a in FIG. 3C so as to cure the insulation adhesion circled by the dashed line b in FIG. 3C by ultraviolet rays. Thus, the configuration may be employed in which the insulation adhesive has an ultraviolet curing property and part of the insulation adhesive layer 32, which is mechanically coupled with a part, on which the terminals 42 are not formed, of the surface of the microphone 40 (a part of the bottom surface 40a), is locally cured by ultraviolet rays.

Alternatively, as another employable configuration, an insulation adhesive having an ultraviolet curing property may be used as the insulation adhesive layer 32 as above and the whole of the insulation adhesive layer 32 may be irradiated with ultraviolet rays and cured by ultraviolet rays. Here, the whole of the insulation adhesive layer 32 which is cured by ultraviolet rays maintains flexibility, can elastically deform, and further, does not lose the adhesion of the surface thereof. Since a process of ultraviolet ray curing can be easily completed by using a surface irradiation type ultraviolet ray irradiation device in this configuration, this configuration is more easily manufactured than the configuration in which ultraviolet ray curing is locally performed as described above. Further, if ultraviolet ray curing is performed in a state that the cover film 50 is disposed, the cover film 50 is rendered to be bonded to the base member with wiring 30 on the whole surface, which comes into contact with the insulation adhesive layer 32, thereof.

An insulation adhesive having the ultraviolet curing property is obtained by including a polymerizable compound in the above-mentioned polymer used as the insulation adhesive. Examples of the polymerizable compound include a radical polymerizable compound having a radical polymerizable functional group such as monofunctional acrylate, multifunctional acrylate, maleimide, thiol, and vinyl ether.

Examples of a radical polymerization initiator include a radical polymerization initiator for generating initiating radical by one molecule and a radical polymerization initiator for generating radical by reaction between two molecules. Examples of the polymerization initiator for generating initiating radical by one molecule include compounds such as acetophenone, acylphosphine, titanocene, triazine, and bisimidazole. Further, examples of the polymerization initiator for generating radical by reaction between two molecules include compounds such as benzophenone, amine, and thioxanthone.

Meanwhile, the film 31 may have stretchability in addition to flexibility. If the film 31 has stretchability, the film 31 can be brought into close contact with a surface of a solid, which is a sound detection object, in a favorable manner irrespective of the shape of the solid. In this case, the cover film 50 and the conductor pattern 33 also are assumed to have stretchability.

As a material of the film 31 and the cover film 50 having stretchability, polyurethane-based, styrene-based, olefin-based, polyester-based, polyamide-based, and silicone-based elastomers or ethylene-propylene-based, nitrile-butadiene-based, silicone-based, acrylic-based, fluorine-based, and urethane-based synthetic rubber, for example, can be used.

Further, as a material of the conductor pattern 33 having stretchability, the above-mentioned elastomers which have stretchability and in which a metal material such as silver or copper or a conductive material such as carbon is dispersed can be used.

INDUSTRIAL APPLICABILITY

The film surface sound receiving type sound sensor module according to the present invention is applicable to grasping of, based on sound, states of various types of solids such as a human body, a device, and a structural object. As concrete examples, the film surface sound receiving type sound sensor module is applicable to nondestructive inspection based on hammering, diagnosis based on auscultation, and the like and can be used instead of perception and diagnosis by human beings.

Further, various sound signals can be acquired by changing a property of a film, and a state of a solid can be more beneficially grasped based on sound by analyzing a correlation between a film property and sound data.

What is claimed is:

1. A sound sensor module for receiving sound through a film, the sound sensor module comprising:
    a base member comprising:
        an elastically-deformable insulation adhesive layer and;
        a conductor pattern on one surface of the insulation adhesive layer, wherein the film on the other surface of the insulation adhesive layer has flexibility; and
    a microphone having a terminal and a sound hole, wherein the microphone is attached to the one surface of the insulation adhesive layer with the terminal being in touch with the conductor pattern in face-to-face manner and with the sound hole covered by the one surface of the insulation adhesive layer.

2. The sound sensor module according to claim 1, wherein
    the insulation adhesive layer is made of an insulation adhesive having an ultraviolet curing property, and
    the insulation adhesive layer has a part cured by ultraviolet light, to which the microphone is attached.

3. The sound sensor module according to claim 2, wherein a whole of the insulation adhesive layer is a layer cured by ultraviolet light.

4. The sound sensor module according to claim 1, wherein the base member has a flexible cover film covering the one surface of the insulation adhesive layer and a part of the conductive pattern, except for an area to which the microphone is attached.

5. The sound sensor module according to claim 2, wherein the base member has a flexible cover film covering the one surface of the insulation adhesive layer and a part of the conductive pattern, except for an area to which the microphone is attached.

6. The sound sensor module according to claim 3, wherein the base member has a flexible cover film covering the one surface of the insulation adhesive layer and a part of the conductive pattern, except for an area to which the microphone is attached.

* * * * *